(12) United States Patent
Tambasco, Jr. et al.

(10) Patent No.: US 10,607,727 B2
(45) Date of Patent: Mar. 31, 2020

(54) AUTOMATIC GENERATION OF PATIENT PRESENCE FOR PATIENT PORTALS

(71) Applicant: Access My Records, Inc., Boca Raton, FL (US)

(72) Inventors: Leonard J. Tambasco, Jr., Boca Raton, FL (US); Scott G. Kinnear, Deerfield Beach, FL (US)

(73) Assignee: Access My Records, Inc., Boca Raton, FL (US)

( * ) Notice: Subject to any disclaimer, the term of this patent is extended or adjusted under 35 U.S.C. 154(b) by 976 days.

(21) Appl. No.: 14/313,766

(22) Filed: Jun. 24, 2014

(65) Prior Publication Data

US 2015/0370969 A1    Dec. 24, 2015

(51) Int. Cl.
*G16H 10/60* (2018.01)

(52) U.S. Cl.
CPC .................................. *G16H 10/60* (2018.01)

(58) Field of Classification Search
CPC ........ G06Q 50/22; G06Q 50/24; G16H 10/60; G06F 19/00; G06F 19/30; G06F 19/32; G06F 19/34
See application file for complete search history.

(56) References Cited

U.S. PATENT DOCUMENTS

| | | | |
|---|---|---|---|
| 7,593,013 B2 * | 9/2009 | Agutter | G06F 17/30554 345/440 |
| 8,738,687 B2 * | 5/2014 | Nakajima | H04L 12/2836 709/203 |
| 2002/0147389 A1 * | 10/2002 | Cavallaro | A61B 5/044 600/301 |
| 2005/0043827 A1 * | 2/2005 | Schaeffer | G06Q 10/10 700/72 |
| 2008/0219524 A1 * | 9/2008 | Brackett | G06F 19/321 382/128 |
| 2009/0024417 A1 * | 1/2009 | Marks | G06Q 50/22 705/3 |
| 2009/0228303 A1 * | 9/2009 | Faulkner | G06Q 50/22 705/3 |

(Continued)

*Primary Examiner* — Jonathan Ng
*Assistant Examiner* — Amanda R. Covington
(74) *Attorney, Agent, or Firm* — Fleit Intellectual Property Law; Thomas S. Grzesik

(57) ABSTRACT

Various embodiments automatically generate a patient presence for a patient portal. In one embodiment, a secure communication is received from at least one electronic health management system. The secure communication comprises at least patient identifying information associated with a given individual. A set of user profiles associated with the patient portal is analyzed based on the patient identifying information. A determination is made, based on the analyzing, that the given individual fails to include an account with the patient portal. The given individual is automatically registered with the patient portal based on the determination. A communication is automatically sent to at least one of the electronic health management system and the given individual, and includes at least the login identifier, the password. The communication notifies the at least one of the electronic health management system and the given individual that the given individual has been automatically registered with the portal.

17 Claims, 8 Drawing Sheets

(56) References Cited

U.S. PATENT DOCUMENTS

| | | | |
|---|---|---|---|
| 2009/0254971 A1* | 10/2009 | Herz | G06Q 10/10 |
| | | | 726/1 |
| 2009/0327666 A1* | 12/2009 | Wolczko | G06F 9/30032 |
| | | | 712/225 |
| 2011/0054934 A1* | 3/2011 | Vesto | G06Q 10/06 |
| | | | 705/3 |
| 2012/0239413 A1* | 9/2012 | Mathur | G06Q 50/22 |
| | | | 705/2 |
| 2013/0144637 A1* | 6/2013 | Bertha | G06F 19/3456 |
| | | | 705/2 |
| 2017/0109478 A1* | 4/2017 | Hasan | G06F 19/324 |
| 2017/0308829 A1* | 10/2017 | Li | G06Q 10/0635 |

* cited by examiner

| | | | |
|---|---|---|---|
| Patient Name: Jane Doe | Patient Age: 35 | | Gender: Female |
| Insurance: Company_A | PCP: Dr._A | | |
| Summary | Past Medical History | Past Surgical History | Current Medication |
| Vitals | 320 | 322 | 324 |
| Prescriptions | | | |
| Assessments | | | |
| · | | | |
| · | Allergy Information | Social History | Family History |
| · | | | |
| Radiology Reports | 326 | 328 | 330 |
| · | | | |
| · | | | |
| Labe Results | · · · | · · · | · · · |

| Facility ID 528 | Login 510 | Password 512 | Address 514 | Contact 516 | Billing Data 518 | Patients 520 | Subscriber ID 521 | ... |
|---|---|---|---|---|---|---|---|---|
| FacID_1 522 → 502 | UserName_1 524 | Passw_1 526 | Addr_A 528 | Contact_A 530 | Billing_1 532 | PatID_1 ... PatID_Y 534 | Sub_1 536 | ... |
| FacID_2 → 504 | UserName_2 | Passw_2 | Addr_B | Contact_B | Billing_2 | ... | Sub_2 | ... |
| FacID_N → 506 | UserName_N | Passw_N | Addr_N | Contact_N | Billing_N | ... | Sub_N | ... |

FIG. 9

| Subscriber ID 908 | Login 910 | Password 912 | Address 914 | Contact 916 | Billing Data 918 | Patients 920 | Facility ID 921 | ... |
|---|---|---|---|---|---|---|---|---|
| Sub_1 920 → 902 | UserName_A 924 | Passw_A 926 | Addr_1 922 | Contact_1 920 | Billing_A 932 | PatID_1 ... PatID_M 934 | FacID_1 | ... |
| Sub_2 → 904 | UserName_B | Passw_B | Addr_2 | Contact_2 | BillBg_2 | ... | Facility_Y Facility_2 | ... |
| Sub_N → 906 | UserName_M | Passw_M | Addr_M | Contact_M | Billing_M | ... | FacID_N | ... |

900

| Patient ID | Record IDs | Login | Password | Contact Information | Prefs | Billing Data | Facility | Subscriber | ... |
|---|---|---|---|---|---|---|---|---|---|
| 608 | 610 | 612 | 614 | 616 | 618 | 620 | 622 | 623 | |
| PatID_1 624 | Rec_ID_A ... Rec_ID_D | Login_A 628 | Pwrd_A 630 | Con_Inf_1 632 | Prefs_A 634 | Billing_1 636 | FacID_1 | Sub_1 | ... |
| PatID_2 | Rec_ID_E ... Rec_ID_H 626 | Login_B | Pwrd_B | Con_Inf_2 | Prefs_B | Billing_2 | ... FacID_M 638 | ... Sub_Y Sub_2 640 | ... |
| ... | ... | | | ... | ... | ... | ... | ... | ... |
| PatID_N | Rec_ID_N | Login_N | Pwrd_N | Con_Inf_N | Prefs_C | Billing_X | ... | Sub_N | ... |

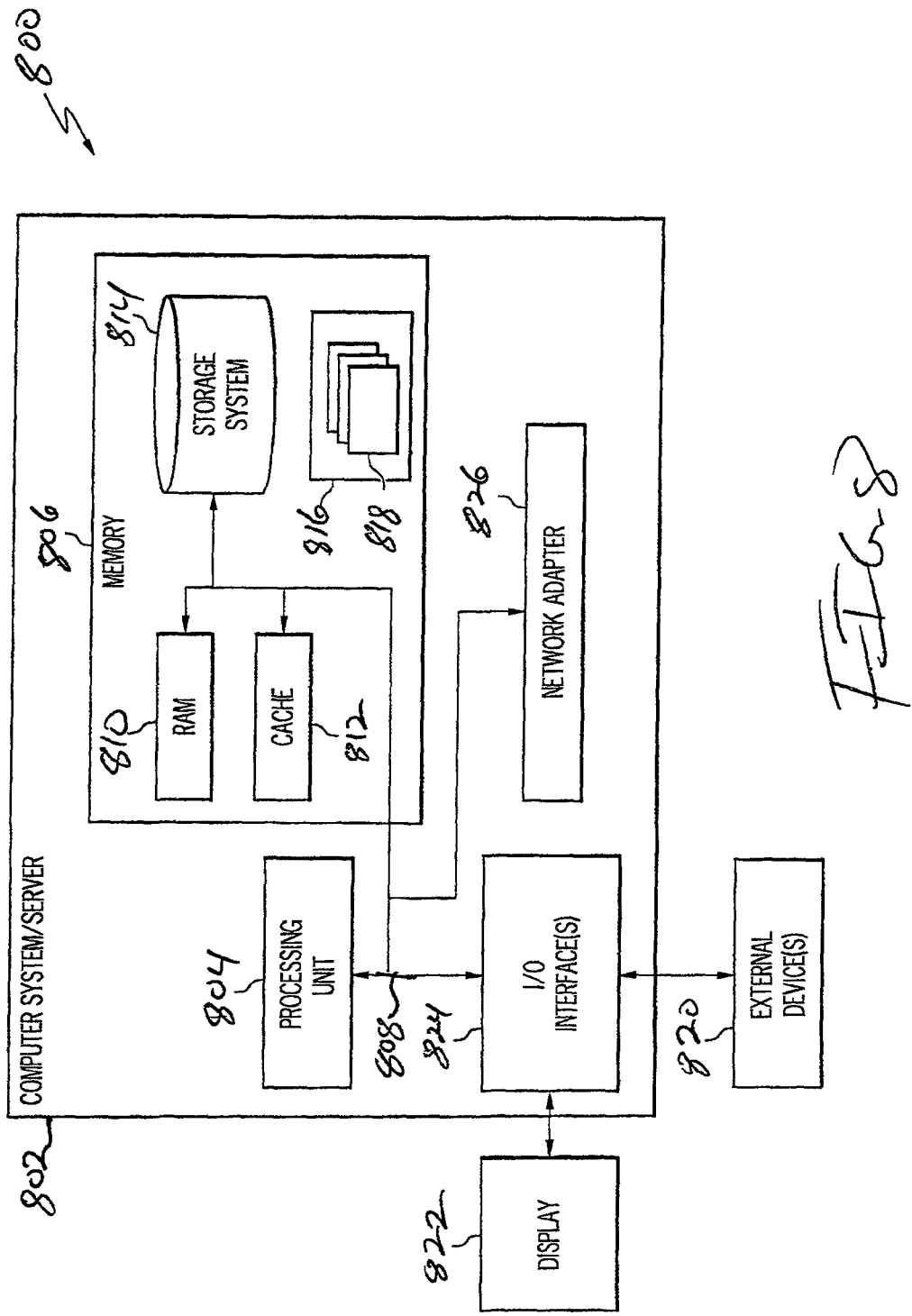

AUTOMATIC GENERATION OF PATIENT PRESENCE FOR PATIENT PORTALS

BACKGROUND

The present disclosure generally relates to the electronic management of health/medical records, and more particularly relates to automatically generating a presence for a patient within a patient portal.

Healthcare providers have traditionally maintained all of their patients' information in paper filing systems. However, this practice is very inefficient and lends itself to poor management practices of the patient's data. Accordingly, Electronic Health Management Systems (EHMS) have been developed to provide many of the functionalities and features of paper filing systems in an electronic paperless format. These systems streamline workflow processes and clinical, financial, and administrative information. Electronic Health Management Systems also improve coding and billing accuracy.

BRIEF SUMMARY

In one embodiment, a method for automatically generating a patient presence for a patient portal is disclosed. The method comprises receiving a secure communication from at least one electronic health management system. The secure communication comprises at least patient identifying information associated with a given individual. A set of user profiles associated with the patient portal is analyzed based on the patient identifying information. A determination is made, based on the analyzing, that the given individual fails to include an account with the patient portal. The given individual is automatically registered with the patient portal based on the determination. A communication is automatically sent to at least one of the electronic health management system and the given individual, and includes at least the login identifier, the password. The communication notifies the at least one of the electronic health management system and the given individual that the given individual has been automatically registered with the patient portal.

In another embodiment, an information processing system for automatically generating a patient presence for a patient portal is disclosed. The information processing system comprises memory and a processor that is communicatively coupled to the memory. The information processing system further comprises a health care patient portal. A patient portal manager is communicatively coupled to the memory and the processor. The patient portal manager is configured to perform a method. The method comprises receiving a DIRECT message from at least one electronic health management system. The DIRECT message comprising structured data in a continuity of care document. The structured data comprises at least patient identifying information associated with a given individual and health-related information associated with the individual. A set of user profiles associated with the patient portal is analyzed based on the patient identifying information. A determination is made, based on the analyzing, that the given individual fails to include an account with the patient portal. The given individual is automatically registered with the patient portal based on the determination. A communication is automatically sent to at least one of the electronic health management system and the given individual, and includes at least the login identifier, the password. The communication notifies the at least one of the electronic health management system and the given individual that the given individual has been automatically registered with the patient portal.

In yet another embodiment, a computer program storage product for automatically generating a patient presence for a patient portal is disclosed. The computer program storage product comprising instructions configured to perform a method. The method comprises receiving a secure communication from at least one electronic health management system. The secure communication comprises at least patient identifying information associated with a given individual. A set of user profiles associated with the patient portal is analyzed based on the patient identifying information. A determination is made, based on the analyzing, that the given individual fails to include an account with the patient portal. The given individual is automatically registered with the patient portal based on the determination. A communication is automatically sent to at least one of the electronic health management system and the given individual, and includes at least the login identifier, the password. The communication notifies the at least one of the electronic health management system and the given individual that the given individual has been automatically registered with the patient portal.

BRIEF DESCRIPTION OF THE SEVERAL VIEWS OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which:

FIG. 3 shows one example of an electronic record according to one embodiment of the present disclosure;

FIG. 5 shows one example of a facility profile for a patient portal according to one embodiment of the present disclosure;

FIG. 6 shows one example of a user profile for a patient portal according to one embodiment of the present disclosure;

FIG. 8 is a block diagram illustrating one example of an information processing system according to one embodiment of the present disclosure; and FIG. 9 shows one example of a subscriber profile for a patient portal according to one embodiment of the present disclosure.

DETAILED DESCRIPTION

Operating Environment

Figure 1:
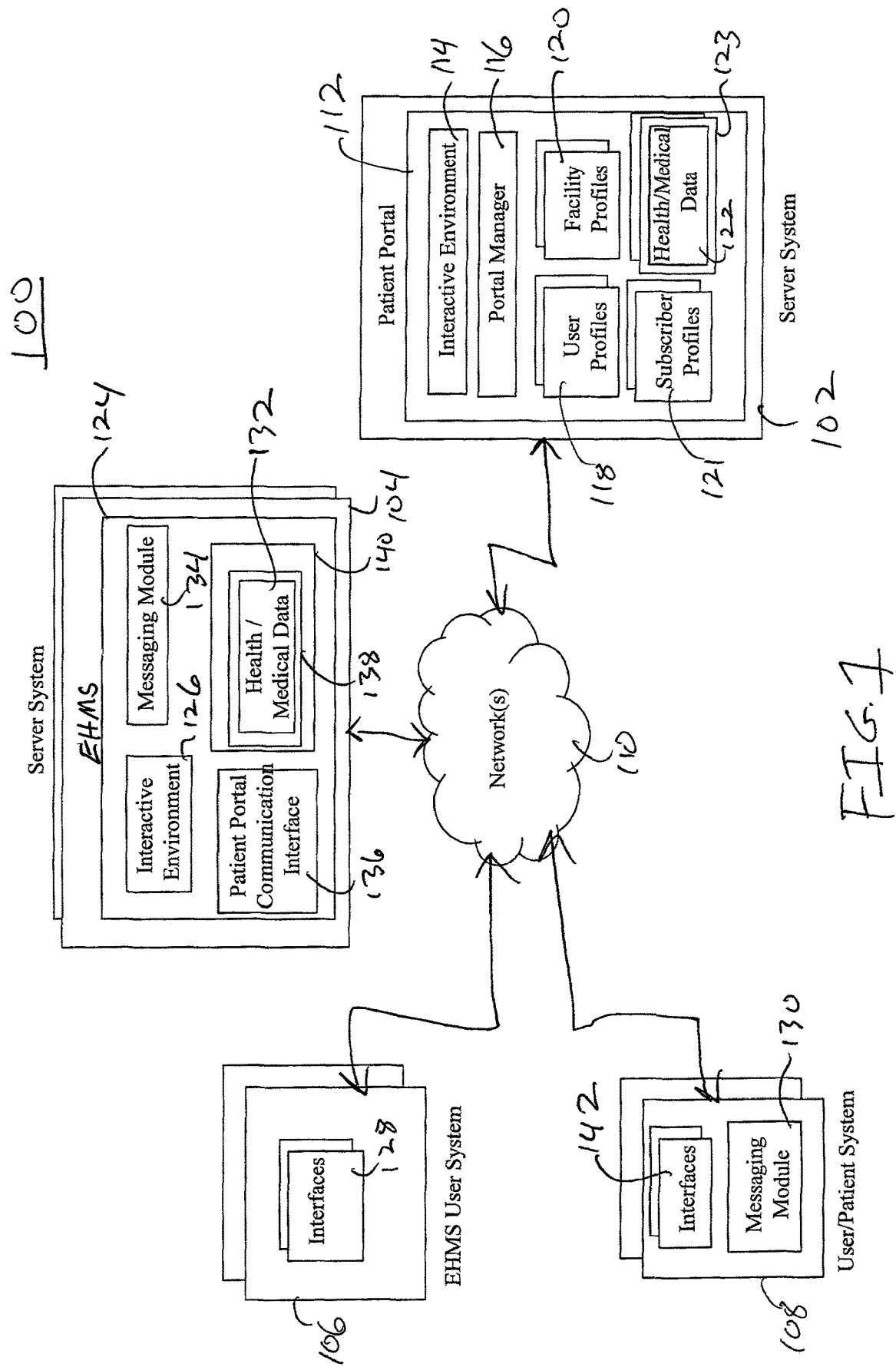
FIG. 1 is a block diagram illustrating one example of an operating environment according to one embodiment of the present disclosure.

FIG. 1 illustrates one example of an operating environment 100 according to one embodiment of the present disclosure. The operating environment 100, in this embodiment, comprises a plurality of information processing systems 102, 104, 106, 108 communicatively coupled to one or more networks 110. The information processing systems 102, 104, 106, 108 comprise server systems, user systems, and/or the like. Examples of user systems include (but are not limited to) desktop computers; servers; portable computing devices such as laptop computers mobile/smart phones, tablets, wearable computing devices (e.g., smart watches), personal digital assistants, etc.; and the like. In one embodiment, one or more of the information processing systems 102, 104, 106, 108 are part of a cloud-computing environment or a non-cloud computing environment.

Figure 2:
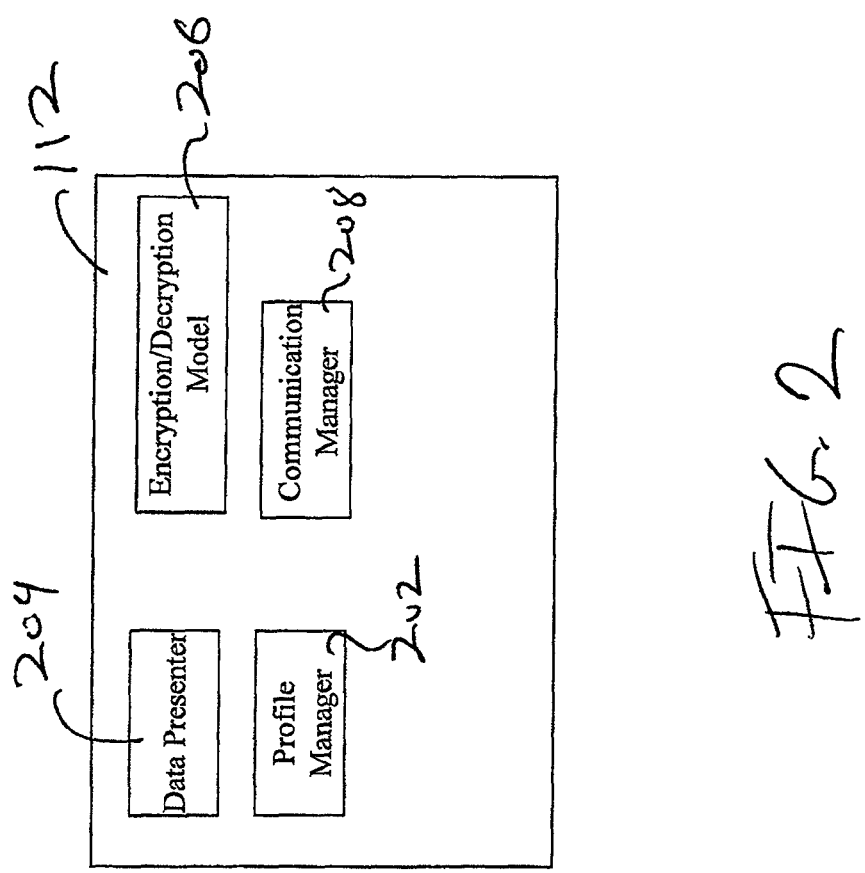
FIG. 2 is a block diagram illustrating a detailed view of a patient portal manager according to one embodiment of the present disclosure.

At least one system 102 comprises a patient portal 112. The patient portal 112 is a healthcare-related website and/or online application (e.g., a cloud-based application) or service (e.g., a cloud-based service) that allows patients to securely manage and view their health information created by one or more health care providers such as physicians and hospitals. The patient portal 112 also allows a registered user patient to securely interact and communicate with their healthcare providers. The patient portal 112 further allows the registered user patient to view, download, and/or transmit patient portal records 123 (or data) and indicate whether the viewed, downloaded, and/or transmitted record (or data) is to be a Continuity of Care Document (CCD) in human-readable format, or a CCDA XML based CCD. In one embodiment, the patient portal 112 comprises an interactive environment 114 and a patient portal manager 116. The patient portal manager 116 comprises a profile manager 202 (FIG. 2), a data presenter 204, a data encryption/decryption module 206, and a communication manager 208. The patient portal 112 further comprises user profiles 118, facility profiles 120, subscriber profiles 121, and user health/medical data 122 stored within one more electronic records 123. Each of these components is discussed in greater detail below. One example of a patient portal 110 is provided in U.S. patent application Ser. No. 14/314,099, entitled "Electronic Management Of Patient Health Care Data" filed on Jun. 25, 2014, which is hereby incorporated by reference in its entirety.

In one embodiment, at last a second of the server systems 104 comprises an electronic record management system such as an Electronic Health Management System (EHMS) 124. It should be noted that an EHMS 124 can also reside on a user system 106 and/or within a local network comprising a user system 106. An EHMS 124 comprises and/or is based on, for example Electronic Medical Record (EMR) Systems, Electronic Health Record (EHR) Systems, Personal Health Record (PHR) Systems, Practice Management Software Systems, Health Information Exchanges (HIEs), and device and software vendors systems in the patient healthcare continuum.

The EHMS 124 comprises an interactive environment that allows healthcare professionals to interact with the EHMS 124 via one or more based interfaces 128 (e.g., a patient portal communication interface, applications, user interfaces, web browsers, and/or the like) residing on their user system 106. The EHMS 124 further comprises, among other things, patient health/medical data 132, a messaging module 134, and an optional patient portal communication interface 126. The patient portal communication interface 136 enables the EHMS 124 to securely communicate with the patient portal 112. The patient health/medial data 132, in one embodiment, is stored within one or more electronic records 138, which are maintained within one or more databases 140. The database(s) 140 can be part of the EHMS 124, separate from the EHMS 124, reside on the server system 104, and/or reside on or across one or more remote information processing systems.

In one embodiment, an EHMS 124 comprising the patient portal communication interface 136 is referred to as an "integrated partner", an "integrated subscriber", and/or as being "integrated" with the patient portal 112. Also, a facility and/or provider that utilizes an EHMS 126 that is registered/integrated with the patient portal 112 is also referred to as an "integrated partner", an "integrated subscriber", and/or as being "integrated" with the patient portal 114. However, embodiments of the present disclosure are not limited to integrated EHMSs, facilities, and providers. The patient portal 114 is also able to communicate with non-integrated EHMSs, facilities, providers. For example, one or more of the information processing systems 104, 106, 108 may comprise patient-related health-medical data stored within one or more records, images, and/or the like. These systems also comprise one or more interfaces (e.g., applications, user interfaces, web browsers, and/or the like). A patient portal communication interface does not reside on these systems and, therefore, these systems are considered to be not integrated with the patient portal 112. However, these systems are able to utilize one or more of their interfaces to transmit and receive unstructured, semi-structured, and/or structured data to/from the patient portal 112.

The EHMS 124 allows a user such as a health care provider to create and manage electronic records 138 for his/her patients. Examples of electronic records 138 include EMRs, EHRs, PHRs, records generated by Practice Management Software Systems, records generated by HIEs, and/or any other types of electronic records generated within the patient healthcare continuum. It should be noted that the terms "Electronic Health Records" and "Electronic Medical Records" can be used interchangeably. EHRs and EMRs are systematic collections of electronic health information associated with a specific individual (patient) or population. An EHR comprises various types of information such as patient medical history, immunization status/history, lab results, medication and allergy information, radiology images, vital signs, personal statistics (e.g., age, weight, and height), demographics, billing information, and/or the like.

An EHR/EMR can be a patient record created in hospitals and ambulatory environments using an Electronic Health Management System (EHMS) 124 either on the network or residing locally at the hospital or ambulatory environment who created the record. An EHR/EMR is generally an internal record generated and maintained within an institution to give patients, physicians and other health care providers, employers, and payers or insurers access to a patient's medical records across facilities. An EHR/EMR software vendor produces software to manage Electronic Health Records for the health care providers use. A PHR is an online accessible health record that is maintained by the patient and comprises health data and information related to the care of the patient. The patient generally provides the information to be maintained by a PHR.

As discussed above, one or more individuals interact with the EHMS 124 via one or more interfaces 128 on a user system 106. In particular, users interact with the interactive environment 126 of the EHMS 124 to enter, store, and manage various medical and health related data/information associated with a given patient (or the user). For example, the user can enter administrative and billing data, patient demographics, progress notes, vital signs, medical histories, diagnoses, medications, immunization dates, allergies, radiology images, lab and test results, and/or the like into the EHMS 124. The EHMS 124 generates and maintains at least one electronic record 138 for the identified patient/user based on the data entered. The EHMS 124 stores and maintains these records 138 in one or more databases 140.

FIG. 3 shows one example of an electronic record(s) 338 generated by the EHMS 124 and displayed to a user of the interactive environment. In this example, the electronic record(s) 338 is an EHR. However, the EHMS 124 is not limited to only generating EHRs and can generate any type of electronic record associated with a patient. FIG. 3 shows the interactive environment 126 being displayed to the user via the interface 128 on his/her system 106. Within the interactive environment 126, an EHR 338 is displayed to the user. The EHR 338 comprises a first portion 302 displaying general patient data such as patient name 304, patient age 306, patient gender 308, patient insurance 310, patient primary care physician 312, and various other types of data. At least a second portion 314 of the EHR 338 displays either all of the health/medical related information associated with the patient or displays a portion of this information as selected by the user. For example, the EHR 338 can be associated with various sections each comprising different types of information such as vitals, lab results, radiology images/reports, prescriptions, assessments, and/or the like. The user is able to select a given section of the EHR 338 generally from a menu/tab option 316 displaying the various sections headings of the EHR 338. In the example shown in FIG. 3, the user has selected a summary section 318. This section 318 displays a patient summary comprising various types of medical/health related information such as past medical history 320, past surgical history 322, current medication 324, allergy information 326, social history 328, family history, 330, and/or the like.

In one embodiment, the EHMS 124 is communicatively coupled to patient portal 112 such that the EHMS 124 is able to transmit electronic records 138 to the portal 112 for patient/user viewing. In one embodiment, the EHMS 124 is configured to automatically transmit a patient's electronic records 138 once they are created or after one or more predefined conditions have occurred. Alternatively, an authorized user such as a healthcare provider manually instructs the EHMS 124 to transmit a patient's electronic records 138 to the patient portal 112. It should be noted that an individual user patient is also able to send their electronic records to the patient portal 112 themselves as well. For example, the user patient is able to instruct the EHMS 124 to send his/her records 138 to the patient portal 112. In another embodiment, the user patient is able to send his/her records and/or any health and medical data directly to the patient portal 112 without involving the EHMS 124.

In one embodiment, the data from an electronic record 138 is transmitted to the patient portal 112 according to one or more standards; however this is not required. In this embodiment, structured and/or unstructured data (including attachments in binary form) comprising patient identifying information, patient health-related information, patient medical-related information, and/or the like is sent to the patient portal 112. For example, an electronic record 138 can be transmitted from the EHRS 124 or the system 108 of an individual user patient as structured and/or unstructured data, a Continuation of Care Record (CCR), a Continuity of Care Document (CCD) or one of its equivalents/permutations, an unstructured clinical document architecture (CDA) record, and/or the like. It should be noted that embodiments of the present disclosure are not limited to such examples, and electronic records 126 or their data can be transmitted to the patient portal in any format.

CCRs and CCDs are both data sets conforming to specific health record standard specifications. A CCR comprises a summary of a patient's health status including medications, allergies, problems, insurance information, care plans, and/or the like. There are six sections of a CCR that have mandated core elements. These sections include a header, patient identifying information, patient financial and insurance information, health status of the patient, care documentation, and care plan recommendation. A CCD document comprises a dataset that conforms to an XML-based markup standard that specifies the semantics, encoding, and structure of a patient summary clinical document. A CCD comprises information such as the "Common MU Data Set", where "MU" stands for Meaningful Use. This data set comprises Patient name, sex, date of birth, race, ethnicity, preferred language, smoking status, problems, medications, medication allergies, laboratory tests, laboratory values/results, vital signs, care plan fields including goals and instructions, procedures and care team members. Other information such as referral reasons, discharge instructions, encounter diagnoses, and immunizations can also be included within a CCD.

Figure 4:
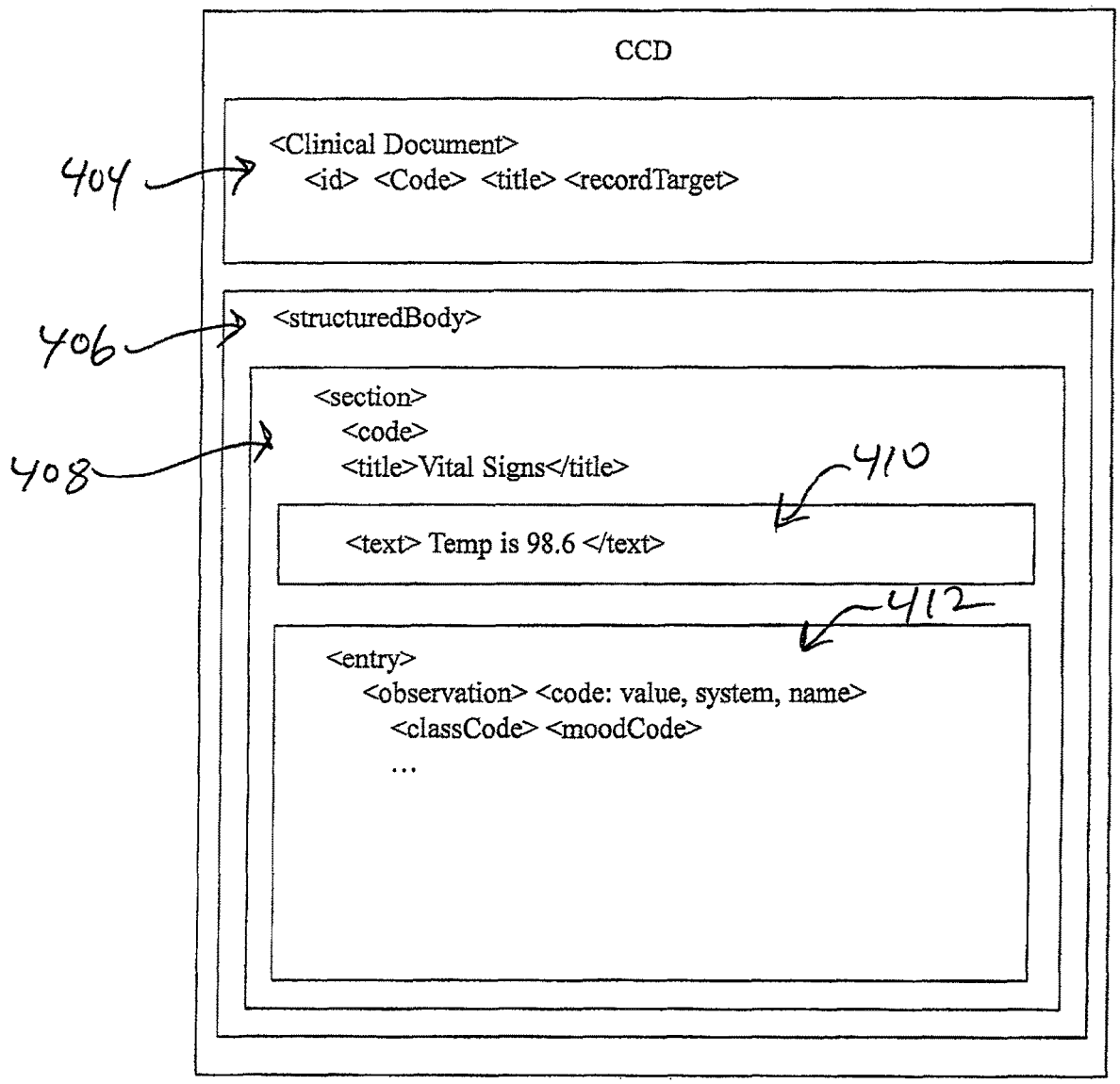
FIG. 4 shows one example of the structure and format of a continuity of care document (CCD)

A CCD document is a human and machine-readable document comprising structured and, optionally, unstructured content. A CCD is generated according to the Clinical Document Architecture (CDA), which is an HL7 authored health care documentation standard. The CDA is a base standard that provides common architecture, coding, semantic framework, and markup language for the creation of electronic clinical documents. FIG. 4 shows one example of the structure and format of a CCD 402. In this example, the CCD comprises a header 404, a body 406, and one or more sections 408. The one or more sections 408 comprise a narrative block 410, and one or more entries 412.

The header 404 sets the context for the CCD as a whole. The header 404 allows management of the CCD and allows it to be exchanged across and within different institutions. The body 406 comprises the clinical report and can comprise structured content that is organized into one or more sections 408. The body 406 can also comprise an unstructured set of data as well. Each section 408 comprises a narrative block 410 and, optionally, one or more coded entries such as medications, allergies, immunizations, vital signs, and problems. Narrative blocks 410 provide human-readability of a CCD. The narrative block within a document section 408 represents the content to be rendered for viewing. Entries 412 provide machine-readability to the CCD. Entries 412 within a document section 408 represent structured content for further computer processing. The EHMS 124 is able to generate a CCD using one or more CDA-based templates. The EHMS 124 can select from one or more header templates, a body templates, and section templates, narrative block templates, and entry templates. Each of these templates is designed to satisfy a specific information exchange scenario and defines the CDA structures to be used to document the applicable clinical information.

When the EHMS 124 detects that an automatic sending condition has occurred or receives an instruction from a user (e.g., healthcare provider or user patient), the EHMS 124 transmits one or more electronic records 138 to the patient portal 112. The electronic records 138, in one embodiment, are transmitted via one or more secured mechanisms; however this is not required. For example, the EHMS 124 and the patient portal 112 are each associated with a security key pair that is used to encrypt/decrypt information being transmitted there between. In addition, the EHMS 124 and the patient portal 112 utilize one or more information exchange technologies such as DIRECT messaging (DIRECT Project), which provide secure messaging between sender and recipient parties, to transmit information between each other. For example, DIRECT messaging can be utilized to send secure emails, secure point-to-point messages (utilizing, for example, the Cross Enterprise Reliable Interchange (XDR) interface), and/or the like between the EHMS 124 and patient portal 112. Secure email utilizes the S/MIME standard for exchanging encrypted emails. With DIRECT messaging, certificates of the sending/receiving parties can be automatically discovered and retrieved across various networks such as the Internet.

In an embodiment where DIRECT messaging is to be used, the EHMS 124 and the patient portal 112 are each associated with a security key pair that is used to encrypt information being transmitted there between. The EHMS 124 and patient portal can send secured messages directly to each other and/or through one or more third-party servers. In an embodiment, where third-party servers are utilized, the EHMS 124 and patient portal 112 are both part of the same or different secured/trust network such as those provided by Healthcare Information Service Providers (HISPs). In this embodiment, the EHMS 124 generates an electronic communication (e.g., email message) comprising an electronic record 138 or its data addressed to a DIRECT messaging address (e.g., DIRECT-messaging-based email address) of the patient portal 112. In one embodiment, the electronic record 138 or its data is packaged in a CCR, CCD or unstructured CDA form; however this is not required.

When utilizing DIRECT messaging, the messaging module 134 of EHMS 124 sends the electronic communication to the patient portal 112 through at least one source trust server. This trust server receives the electronic communication and identifies the destination address, which is the messaging address of the patient portal 112. The trust server identifies the security certificate of the patient portal 112, generates an S/MIME-based message, and signs the message with the private key of the EHMS 124. The trust server further encrypts the message with the certificate (public key) of the patient portal 112 and sends this encrypted message to the patient portal 112.

The patient portal 112 can then receive the electronic communication in its encrypted form and perform decrypting operations itself. Alternatively, a destination trust server can intercept this encrypted communication and perform, for example, an S/MIME decryption process using the private key of the patient portal. After the communication and its content are decrypted, this trust server verifies the communication using a certificate (public key) of the EHMS 124. Once verified, the destination trust server sends the decrypted communication with its content to the patient portal 112 using its DIRECT messaging address. The patient portal 112 receives the communication from the EHMS 124 along with the electronic record/data in an unencrypted form.

In another embodiment, the third-party servers are not required. For example, the EHMS 124 and the patient portal can securely communication directly with each other. In this embodiment, the messaging module 134 of the EHMS 124 implements or is communicatively coupled to the patient portal communication interface 136. In one embodiment, the communication interface 136 utilizes standard web services protocols that transfer messages in a markup language format. These messages can be transmitted over HTTP or another protocol. The communication interface 136, in one embodiment, utilizes one or more security technologies such as SSL (Security Socket Layer) over HTTPS to securely communicate and encrypt the data exchange and communications between the EHMS 124 and the patient portal 112. The communication interface 136 utilizes one or more information exchange technologies such as DIRECT messaging to transmit electronic records to the patient portal 112.

In one embodiment, the messaging module 134 notifies the patient portal 112 via the communication interface 136 that it would like to establish a secure communication link with the portal. Then, either the messaging module 134 or the communication manager 208 of the portal 112 establishes the requested secure communication link. For example, the EHMS 124, in one embodiment, has previously registered with the patient portal 112. In this embodiment, when the messaging module 134 of the EHMS 124 wants to establish a secure connection with the patient portal 112 it provides authentication information via the communication interface 136 to the portal 112 to obtain a security token for that session period. For example, the messaging module 134 of the EHMS 124 sends the following message to the patient portal 112:

```
<?xml version="1.0" encoding="utf-8"?>
<soap12:Envelope xmlns:xsi="http://www.w3.org/2001/XMLSchema-instance"
xmlns:xsd="http://www.w3.org/2001/XMLSchema"
xmlns:soap12="http://www.w3.org/2003/05/soap-envelope">
    <soap12:Body>
        <AuthenticateInterface xmlns="http://tempuri.org/">
            <FacilityId>long</FacilityId>
            < UserLogin>string</ UserLogin>
            <Password>string</Password>
        </AuthenticateInterface>
    </soap12:Body>
</soap12:Envelope>
```

This message/request includes the identifier of the facility (e.g., healthcare provider) associated with the transmission, the login associated with the facility for the patient portal, and the password associated with the facility for the patient portal. The patient portal 112 receives this message and the communication manager 208 analyzes a set of facility profiles 120 to determine if the requesting facility has been previously registered. FIG. 5 shows various examples of facility profiles 120. In the example shown in FIG. 5, each row 502, 504, 506 in the table 500 corresponds to a facility profile. It should be noted that in other embodiments, each facility profile 502, 504, 506 is stored separate from one another. The table 500 comprises a plurality of columns, each storing a different set of information. In this example, the table 500 comprises a first column 508 entitled "Facility ID"; a second column 510 entitled "Login"; a third column 512 entitled "Password", a fourth column 514 entitled "Address"; a fifth column 516 entitled "Contact"; a sixth column 518 entitled "Billing Data"; a seventh column 520 entitled "Patients"; and an eighth column 521 entitled "Subscriber ID"

The "Facility ID" column 508 comprises entries 522 uniquely identifying the facility (e.g., healthcare provider) associated with the facility profile. The "Login" column 510 comprises entries 524 with the unique login or user name assigned to the facility for interacting with the patient portal. The "Password" column 512 comprises entries 526 with the unique password assigned to the facility for interacting with the patient portal 112. The "Address" column 514 comprises entries 528 with the address of the facility. The "Contact" column 516 comprises entries 530 that identify the contact person at the facility who manages the facility's account with the patient portal. The "Billing Data" column 518 comprises entries 532 with various types of billing data associated with the facility (if applicable). Examples of billing data include subscription plan type, payment information, payment histories, and/or the like. The "Patients" column 520 comprises entries 534 with the patient ID (or a pointer to the user profile 118) of each patient associated with the facility. The "Subscriber ID" column 521 comprises entries 536 with the subscriber ID of the EHMS 124 associated with the facility. It should be noted that one or more of the columns and entries shown in FIG. 5 are optional, and additional information can be included within a facility profile 120 as well.

In another embodiment, the authentication request/message received from the EHMS 124 includes information associated with the EHMS 124 in addition to or in place of the facility information. For example, the authentication request/message comprises the identifier of the EHMS 124 associated with the transmission, the login associated with the EHMS 124 for the patient portal, and/or the password associated with the EHMS 124 for the patient portal. The patient portal 112 receives this message and the communication manager 208 analyzes a set of subscriber profiles 121 to determine if the requesting facility has been previously registered. FIG. 9 shows various examples of subscriber profiles 121. In the example shown in FIG. 9, each row 902, 904, 906 in the table 900 corresponds to a subscriber profile. It should be noted that in other embodiments, each subscriber profile 902, 904, 906 is stored separate from one another. The table 900 comprises a plurality of columns, each storing a different set of information. In this example, the table 900 comprises a first column 908 entitled "Subscriber ID"; a second column 910 entitled "Login"; a third column 912 entitled "Password", a fourth column 914 entitled "Address"; a fifth column 916 entitled "Contact"; a sixth column 918 entitled "Billing Data"; a seventh column 920 entitled "Patients"; and an eighth column 921 entitled "Facility ID".

The "Subscriber ID" column 908 comprises entries 922 uniquely identifying the EHMS associated with the subscriber profile. The "Login" column 910 comprises entries 924 with the unique login or user name assigned to the EHMS for interacting with the patient portal. The "Password" column 912 comprises entries 926 with the unique password assigned to the EHMS for interacting with the patient portal 112. The "Address" column 914 comprises entries 928 with the address of the EHMS. The "Contact" column 916 comprises entries 930 that identify the contact person at the EHMS who manages the EHMS's account with the patient portal 112. The "Billing Data" column 918 comprises entries 932 with various types of billing data associated with the EHMS (if applicable). Examples of billing data include subscription plan type, payment information, payment histories, and/or the like. The "Patients" column 920 comprises entries 934 with the patient ID (or a pointer to the user profile 118) of each patient associated with the EHMS. The "Facility ID" column 921 comprises entries 536 with the subscriber ID of the facilities associated with the EHMS 124. It should be noted that one or more of the columns and entries shown in FIG. 9 are optional, and additional information can be included within a subscriber profile 121 as well. Also, the authentication request/message received from the EHMS 124 can include any type of information that allows the patient portal to identify the facility and/or EHMS 124 associated with the request.

Once the patient portal 112 receives an authentication request message from the EHMS 124, the communication manager 208 analyzes the facility profiles 120 to determine if any of the profiles comprises a facility ID matching the facility ID within the authentication request message. If a match exists, the communication manager 208 further analyzes the profiles 120 to determine if the user name or login information transmitted within the authentication request message matches the information within the identified facility profile. Based on this analysis, the communication manager 208 transmits a response message back to the EHMS 124 via the communication interface 136 of the messaging module 134 either granting the authentication request or denying it. For example, the communication manager 208 sends the following message to the EHMS 124:

```
<?xml version="1.0" encoding="utf-8"?>
<soap12:Envelope xmlns:xsi="http://www.w3.org/2001/XMLSchema-
instance"
xmlns:xsd="http://www.w3.org/2001/XMLSchema"
xmlns:soap12="http://www.w3.org/2003/05/soap-envelope">
    <soap12:Body>
        <AuthenticateInterfaceResponse xmlns="http://tempuri.org/">
            <AuthenticateInterfaceResult>
                <Valid>boolean</Valid>
                <Token>string</Token>
                <ErrorMessage>string</ErrorMessage>
            </AuthenticateInterfaceResult>
        </AuthenticateInterfaceResponse>
    </soap12:Body>
</soap12:Envelope>
```

The above message comprises a "Valid" value if the request from the EHMS 124 was successfully processed; otherwise a "False" value is returned. If the request could not be successfully processed, the message also comprises an error message indicating the reason why the request was denied. If the request was successfully processed the communication manager 208 also sends a security token for the transmission to the EHMS 124. It should be noted that the process above can be similarly performed for authentication of an EHMS 124 as well.

Once the EHMS 124 has obtained a security token, it securely transmits its data to the patient portal 112 over the secured link. For example, the messaging module 134 generates one or more messages/packets comprising an electronic record(s) 128 or its data. The record/data can be packaged as a CCR, CCD, unstructured CDA, and/or the like; however this is not required. The messaging module 134 (or some other module) encrypts the communication with the public key of the patient portal 112 and signs the communication with the private key of the EHMS 124. The messaging module 134 then sends the encrypted communication to the patient portal 112 via secure communication link. It should be noted that the electronic records 138 are not required to be encrypted prior to being sent to the patient portal 112 since the secure communication link provides an encrypted pipe such that the messages are securely encapsulated when being transmitted to the patient portal 112.

In another embodiment, a secure communication link is not established between the EHMS 124 and patient portal 112. In this embodiment, the messaging module 134 of the EHMS 124 securely encrypts the electronic records 138 prior to transmitting them to the patient portal 112. In this embodiment, the messaging module 134 generates a message/packet comprising the encrypted data and sends the message to a messaging address (e.g., email address) of the patient portal. In another embodiment, the EHMS 124 transmits data to the patient portal 112 in an unsecured form over an unsecured link. It should be noted that embodiments of the present disclosure are not limited to the above examples directed to securely transmitting electronic record data to the patient portal 112. Other mechanisms for securely transmitting electronic record data to the patient portal 112 are applicable as well.

It should also be noted that the above discussion is also applicable for sending electronic records/data from a user patient system 108 via a messaging component 130 such as an application, plug-in, web browser, and/or the like residing on a user patient system 108. The user patient system 108 can also comprise one or more interfaces 142 such as the patient portal communication interface discussed above for communicating with the patient portal 112. In addition, a patient is able to utilize a device such as a wireless communication device, a portable electronic device, a desktop computer, and/or the like to capture an image of an object comprising his/her health related information. For example, the patient can have health or medical related data in paper form such as lab results, doctors' records, prescriptions, radiology images, radiology reports, physical therapy treatment plans, hand written health or medical related information, and/or the like.

The patient is able to utilize a camera, scanner, and/or the like to capture in an image of these items, and transmit the image to the patient portal 112 for processing. Alternatively, the patient's device 108 can also process the image and send health-related data items to the patient portal. In embodiments where the patient portal communication interface of the patients device 108 does not perform any image processing and transmits the entire captured image to the patient portal 112 for processing, the patient portal 112 comprises an image analyzer that analyzes the image to identify patient identifying information, healthcare provider and facility information, and/or health/medical related information from the image. The patient transmits his/her health or medical related information to the patient portal via one via one or more communication mechanisms such as via an email message, a SMS message, a MMS message, a DIRECT message, by uploading to the portal 112 through a web browser, transmission through a dedicate portal application residing on the user's system 108, and/or the like. A more detailed discussion on one more examples of a patient transmitting health-related data to the patient portal 112 is given in the co-pending U.S. patent application Ser. No. 14/314,118, entitled "User-Based Remote Capturing Of Health And Medical Related Data" filed on Jun. 25, 2014, which is incorporated by reference in its entirety.

It should be noted that embodiments of the present disclosure are not limited to a facility, EHMS, and/or a user that has been previously registered with the patient portal 112. For example, the patient portal 112 is configured to receive communications from unregistered EHMSs (and users) the same way it receives messages from registered EHMSs (and users) since the portal 112 is able to receive communications at a specific messaging address. In this embodiment, the patient portal 112 identifies a facility, EHMS, and/or a user as being unregistered and provides a security token indicating this. The EHMS (or user) uses this token when sending secured communications to the portal 112. This allows any user patient, regardless of whether their healthcare provider's EHMS is registered with the portal 112, to be able to access their health/medical information via the patient portal 112.

In another embodiment, if the communication manager 208 determines that a facility and/or an EHMS 124 does not have an account with the patient portal 112 the portal manager 116 automatically creates an account/presence for the facility and/or an EHMS 124. Stated differently, the portal manager 116 automatically registers the facility and/or an EHMS 124 with the patient portal 112 and creates an account for this facility and/or an EHMS 124. This auto-creation of an account/presence for the facility and/or an EHMS 124 is based on the portal 112 receiving a message (e.g., DIRECT message) or other communication from an EHMS 124 comprising one or more electronic health/medical records, where either the facility associated with the message is unregistered and/or the EHMS 124 sending the message is unregistered. The profile manager 202 generates a facility profile 120 for an unregistered facility and/or generates a subscriber profile 121 for an unregistered EHMS 124. The profile manager 202 populates the generated profile(s) with at least a unique identifier for the facility and/or EHMS 124, respectively. The portal manager 116 can also generate authentication information such as login username and password. This authentication information can be transmitted back to the EHMS 124 using a secure transmission mechanism such as DIRECT messaging or an unsecured transmission method. Alternatively, the portal manager 116 can send a message/communication to the EHMS 124 notifying it that the facility and/or the EHMS 124 has been automatically registered with the patient portal 112, and that a user needs to login to the patient portal to setup the account.

When the patient portal 112 receives a secured transmission (e.g., an encrypted message) from the EHMS 124, the encryption/decryption module 206 decrypts the message (e.g., using its private key). The communication manager 210 can then optionally verify that the message was actually sent by the EHMS 124 by checking the message's secure signature. In other embodiments, the patient portal receives an unencrypted DIRECT message from the EHMS 124 at its protected DIRECT messaging address. This message has been previously decrypted and verified by a third-party authentication/trust server, as discussed above.

The communication manager 210 analyzes the contents of a received message/communication to identify the user patient associated with the record data. In one embodiment, the electronic record 138 transmitted in the message received from the EHMS 124 comprises user patient identifying information such as the patient's name, address, phone number, email address, patient ID for the facility, patient ID for the patient portal (if previously registered), and/or any other type of information that can be used to uniquely identify the patient. The communication manager 210 compares the patient identifying information within the received record 138 to information in one or more user profiles 118.

FIG. 6 shows various examples of user profiles 118. In the example shown in FIG. 6, each row 602, 604, 606 in the table 600 corresponds to a user profile. It should be noted that in other embodiments, each patient profile 602, 604, 606 is stored separate from one another. The table 600 comprises a plurality of columns, each storing a different set of information. In this example, the table 600 comprises a first column 608 entitled "Patient ID"; a second column 610 entitled "Record IDs"; a third column 612 entitled "Login"; a fourth column 614 entitled "Password", a fifth column 616 entitled "Contact Information"; a sixth column 618 entitled "Prefs"; a seventh column 620 entitled "Billing Data"; and eighth column 622 entitled "Facilities", and a ninth column 623 entitled "Subscriber".

The "Patient ID" column 608 comprises entries 624 uniquely identifying the user patient associated with the user profile for the patient portal 112. The "Login" column 610 comprises entries 626 with the unique login or user name assigned to the user patient for interacting with the patient portal 112. The "Record IDs" column 612 comprises entries 628 uniquely identifying each health/medical information record associated with the user and maintain stored by the patient portal 112. These record IDs can also point to a location where the records are stored. In one embodiment, these records are the electronic records 138 received from the EHMS 124 (or the user patient) and/or are records created by the patient portal 112 using the health/medical information within an electronic record 138 received from the EHMS 124 (or the user patient). The patient portal 112 is able to receive electronic records 138 in various different formats, parse and extract their information, and generate its own electronic records 123 based on the extracted information. In this embodiment, the record IDs are associated with and/or pointing to the patient portal generated records 123. This allow the patient portal 112 to receive health-related records and data in any format and process the data independent of the EHMS 124 that sends the record/data.

The "Password" column 614 comprises entries 630 with the unique password assigned to the patient for interacting with the patient portal. The "Contact Information" column 616 comprises entries 632 identifying the contact information of the user patient such as email addresses, home address, phone numbers, and/or the like. The "Prefs" column 618 comprises entries 634 that identify the user patient preferences with respect to the patient portal. For example, the user patient can configure how the patient portal 112 data presenter 204 presents information to the user patient in the patient portal 112. In this example, the user patient is able to select and configure the types of information that are displayed to the user patient in the portal 112. Preferences can also include contact preferences and any other preferences that the user patient is able to configure with respect to the patient portal 112. The "Billing Data" column 620 comprises entries 636 with various types of billing data associated with the patient (if applicable). Examples of billing data include subscription plan type, payment information, payment histories, and/or the like. The "Facility" column 622 comprises entries 638 with the facility ID (or a pointer to the facility profile 120) of each facility associated with the patient. The "Subscriber" column 623 comprises entries 640 with the subscriber ID (or a pointer to the subscriber profile 121) of each EHMS associated with the patient. It should be noted that one or more of the columns and entries shown in FIG. 6 are optional, and additional information can be included within a user profile 118 as well.

As stated above, the communication manager 208 compares the patient identifying information in the electronic record message received from the EHMS 124 (or patient) with the information from the user profiles 118. Based on this comparison, the communication manager 208 determines if the user patient is associated with an account (has been previously registered) for the patient portal 112. If so, the communication manager 208 stores the received electronic record(s) and links them to the patient's account. For example, the portal manager updates the profile associated with the patient with a record ID of this received record(s). In another embodiment, the communication manager 208 manager parses the received EHMS-based record and extracts its data and, optionally, its semantic information and formatting information. The communication manager 208 then creates a patient portal record 123 comprising this extracted information. The user patient's profile 118 is then updated to include the ID of this record 123.

In another embodiment, the communication manager 208 also determines if the facility (e.g., healthcare provider facility such as a specific doctor's office, hospital, laboratory, etc.) and/or the EHMS 124 associated with the received electronic record 138 is currently registered with the portal 112. For example, the communication manager 208 analyzes the facility profiles 120 and the subscriber profiles 121 to identify a profile associated with the facility and/or the EHMS 124 based on the identifier (e.g., login/username) information included within the communication/message received from the EHMS 124.

If a matching facility/subscriber profile is identified, the profile manager 202 links the facility and/or EHMS 124 to the patient if not already linked. For example, if this is the first time the facility and/or the EHMS 124 has submitted data associated with the patient, the profile manager 202 updates the "Patients" column 520, 920 in the facility and/or subscriber profiles with an entry identifying the patient and/or the user profile 118 of the patient. Alternatively, the profile manager 202 can update the "Facilities" and/or Subscriber columns 622, 623 in the user profile 118 of the patient to identify the facility (or its profile) and/or the EHMS (or its profile). If a matching profile 120, 121 is not identified for the facility and/or the EHMS 124 the portal manager 116 automatically registers the facility and/or the EHMS 124 with the portal 112, as discussed above.

In embodiments where the communication manager 208 determines that the user patient does not have an account with the patient portal 112, the portal manager 116 automatically creates an account/presence for the user patient. Stated differently, the portal manager 116 automatically registers the user patient with the patient portal 112 and creates an account for him/her based on receiving a message (e.g., DIRECT message) from an EHMS 124 (or the user patient) comprising one or more electronic health/medical records. The profile manager 202 generates a user profile 118 for the user patient and populates this profile 118 with information extracted from the message received from the EHMS 124. If the facility and/or EHMS 124 that sent the electronic record has been previously registered with the patient portal 112, the profile manager 202 updates the corresponding facility/subscriber profiles 120, 121 to indicate that the facility and/or the EHMS 124 is associated with the user patient. The user profile 118 of the patient can also indicate the facility and/or the EHMS 124 are associated with the user patient. If the facility and/or EHMS 124 have not been previously recorded, the portal manager 116 registers the facility and/or the EHMS 124 with the portal 112 and the profile manager 202 creates a facility and/or subscriber profile 120, 121. These facility, subscriber, and patient profiles can be mapped to each other, as discussed above.

Once the user patient has been automatically registered with the patient portal 112, the communication manager 210 automatically generates a communication (e.g., email) that notifies the user patient (and optionally the EHMS 124) that the user patient has been automatically registered with the patient portal 112. This communication can also comprise the user patient's generated username, generated password, the Uniform Resource Locator (URL) of the patient portal 112, and other information. The communication manager 208 then automatically sends this communication to the EHMS 124 that originally sent the communication comprising this user patient's data. In one embodiment, the communication manager 208 sends the communication to the EHMS 124 using the secure communication methods discussed above; however, this is not required. The EHMS 124 can then relay this account information to the appropriate healthcare provider (or directly to the user patient) that can then provide the account information to the user patient.

In another embodiment, the communication manager 208 addresses the communication to the user patient using the information stored in the newly created profile 118 for the user patient. The communication manager 208 then sends the communication directly to the user patient. In another embodiment, the automatically created communication only comprises the URL of the patient portal 112 and a note indicating that an account has been setup for the user patient. This note can identify the healthcare provider that sent the original message comprising the user patient's record(s). Therefore, the communication does not comprise any personal or confidential information. Once the user patient receives his/her account information, the user patient is able to log into the patient portal 112 and interact with his/her health/medical information. If the user patient is only provided with a URL of the patient portal 112, he/she is prompted to enter identifying information into the patient portal 112 for authentication. Once authenticated, the user is provided with his/her login and password information and/or is able to create his/her own login and password information.

In another embodiment, the patient portal 112 identifies and records the source of the health/medical data 122 used to create the electronic records 138. Stated differently, the patient portal 112 identifies and records whether the health/medical data 122 was received from an integrated partner, a non-integrated entity, or a patient. For example, if the health/medical data 122 was received from a patient, the patient portal 112 assigns a source type of "patient entered" to the electronic records 138. If the health/medical data 122 was received from an integrated partner, the patient portal 112 assigns a source type of "integrated partner" to the health/medical data 122. The identifier and/or the name of the subscriber/facility that sent the health/medical data 122 can also be assigned to the record/data as the source type as well. If the electronic records 138 were received from a non-integrated entity, the patient portal 112 assigns a source type of "non-integrated" to the health/medical data 122. The identifier and/or the name of the non-integrated subscriber/facility that sent the health/medical data 122 can also be assigned to the health/medical data 122 as the source type as well. The source type can be added as an annotation to the stored health/medical data 122, added as a field in the records 123, and/or the like. If the patient portal 112 generates a record 123 from the health/medical data 122 extracted from a communication, the assigned source type is included within this record 123.

It should be noted that instead of (or in addition to) a source type being assigned to received health/medical data 122, the patient portal 112 can store the health/medical data 122 (and records 123) in a section of memory/storage that is allocated for a given source type. For example, a first portion of storage can be allocated for health/medical data 122 received from integrated partners. A second portion of storage can be allocated for health/medical data 122 received from non-integrated partners. A third portion of storage can be allocated for health/medical data 122 received from patients. Therefore, the patient portal 112 is able to determine the source type of stored health/medical data 122 based on which portion of storage they are maintained in. Then, when the user interacts with his/her health/medical information the patient portal 112 may group and present the health/medical data 122 and records 123 associated with the user based on their assigned source type. For example, the patient portal 112 displays a first area comprising health/medical data 122 and records 123 from integrated partners, a second area comprising health/medical data 122 and records 123 from non-integrated entities, and a third area comprising health/medical data 122 and records 123 provided by the patient.

Operational Flow Diagrams

Figure 7:
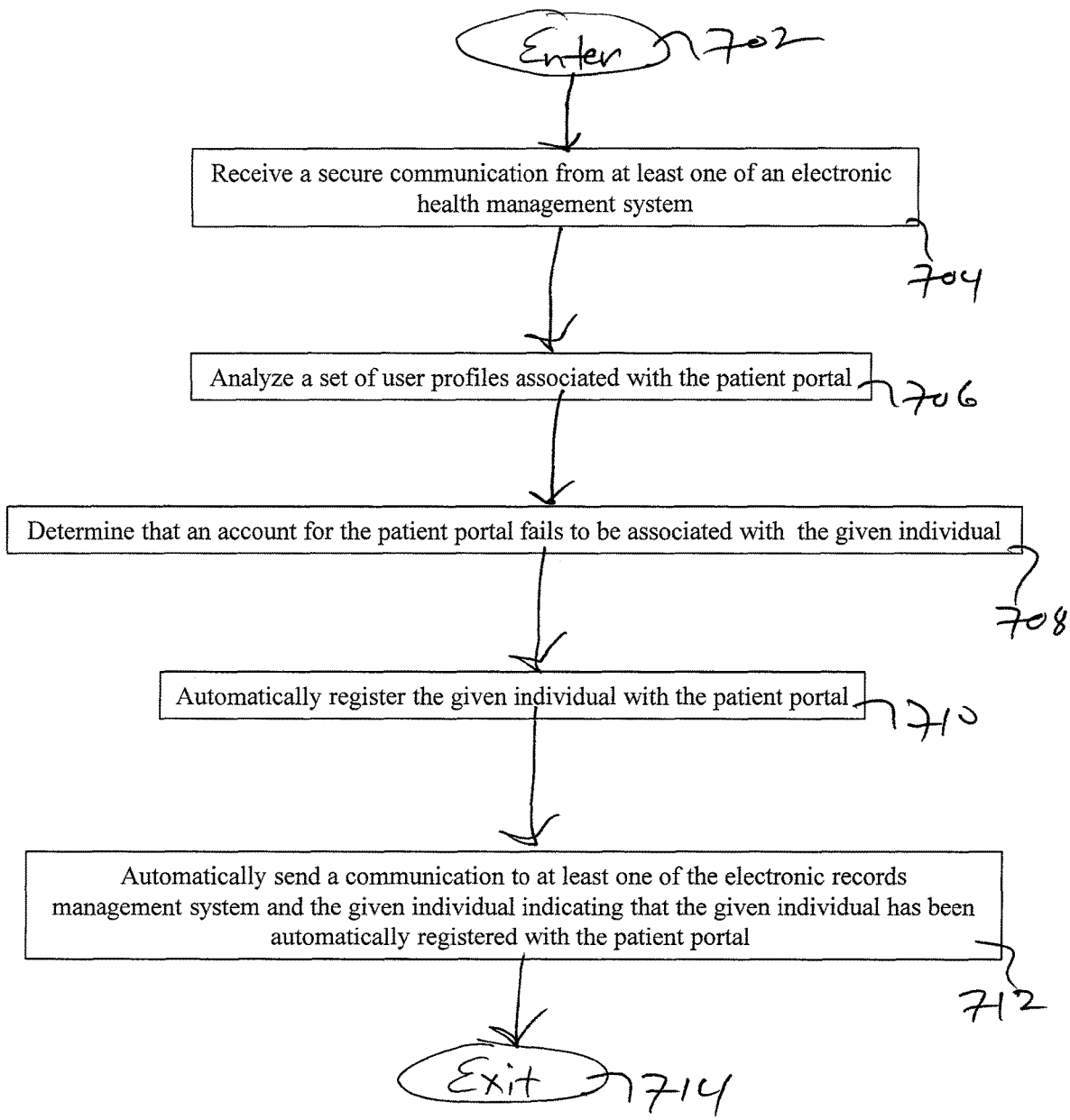
FIG. 7 is an operational flow diagram illustrating one example of an overall process for automatically generating a patient presence for a patient portal according to one embodiment of the present disclosure.

FIG. 7 is an operational flow diagram illustrating one example of an overall process for generating a patient presence for a patient portal 112. The operational flow of FIG. 7 beings a step 702 and flows DIRECT to step 704. The portal manager 116, at step 704, receives a secure communication from at least one electronic health management system 124. The secure communication comprises at least patient identifying associated with a given individual. The portal manager 116, at step 706, analyzes a set of user profiles 118 associated with the patient portal 112 based on the patient identifying information. The portal manager 116, at step 708, determines, based on the analyzing, that an account for the patient portal 112 fails to be associated with the given individual. The portal manager 116, at step 710, automatically registers, based on the determining, the given individual with the patient portal 112 utilizing at least the patient identifying information from the secure communication. The automatic registration of the given individual comprises at least generating a user profile 1118 for the given individual based on at least the patient identifying information. The portal manager 116, at step 712, automatically sends a secure communication to at least one of the electronic health management system 124 and the given individual. The communication notifies the at least one of the electronic health management system and the given individual that the given individual has been automatically registered with the patient portal 112. The control flow ends at step 714.

Information Processing System

FIG. 8 shows a block diagram illustrating an information processing system 800 that can be utilized in various embodiments of the present disclosure such as the information processing system 102 shown in FIG. 1. The information processing system 802 is based upon a suitably configured processing system configured to implement one or more embodiments of the present disclosure. Any suitably configured processing system can be used as the information processing system 802 in embodiments of the present disclosure. The components of the information processing system 802 can include, but are not limited to, one or more processors or processing units 804, a system memory 806, and a bus 808 that couples various system components including the system memory 806 to the processor 804.

The bus 808 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Although not shown in FIG. 8, the main memory 806 includes at the patient portal 112, its components, the user profiles 118, and the facility profiles 120 shown in FIG. 1. The portal manager 116 can reside within the processor 804, or be a separate hardware component. The system memory 806 can also include computer system readable media in the form of volatile memory, such as random access memory (RAM) 808 and/or cache memory 812. The information processing system 802 can further include other removable/non-removable, volatile/non-volatile computer system storage media. By way of example only, a storage system 814 can be provided for reading from and writing to a non-removable or removable, non-volatile media such as one or more solid state disks and/or magnetic media (typically called a "hard drive"). A magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 808 by one or more data media interfaces. The memory 806 can include at least one program product having a set of program modules that are configured to carry out the functions of an embodiment of the present disclosure.

Program/utility 816, having a set of program modules 818, may be stored in memory 806 by way of example, and not limitation, as well as an operating system, one or more application programs, other program modules, and program data. Each of the operating system, one or more application programs, other program modules, and program data or some combination thereof, may include an implementation of a networking environment. Program modules 818 generally carry out the functions and/or methodologies of embodiments of the present disclosure.

The information processing system 802 can also communicate with one or more external devices 820 such as a keyboard, a pointing device, a display 822, etc.; one or more devices that enable a user to interact with the information processing system 802; and/or any devices (e.g., network card, modem, etc.) that enable computer system/server 802 to communicate with one or more other computing devices. Such communication can occur via I/O interfaces 824. Still yet, the information processing system 802 can communicate with one or more networks such as a local area network (LAN), a general wide area network (WAN), and/or a public network (e.g., the Internet) via network adapter 826. As depicted, the network adapter 826 communicates with the other components of information processing system 802 via the bus 808. Other hardware and/or software components can also be used in conjunction with the information processing system 802. Examples include, but are not limited to: microcode, device drivers, redundant processing units, external disk drive arrays, RAID systems, tape drives, and data archival storage systems.

Non-Limiting Examples

As will be appreciated by one skilled in the art, aspects of the present disclosure may be embodied as a system, method, or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit", "module", or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. Also, the phrase "such as" is not intended to limit the disclosure to any particular item being referred to. It will be further understood that the terms "comprises" and/or "comprising" when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. An information processing system for automatically generating a patient presence for a health care patient portal, the information processing system comprising:
   memory;
   a processor communicatively coupled to the memory;
   a health care patient portal; and
   a patient portal manager communicatively coupled to the memory and the processor,
   wherein the patient portal manager is configured to perform a method comprising:
      receiving a plurality of secure communications from a plurality of health-related information sources via one or more external information processing systems, where each secure communication of the plurality of secure communications comprises at least one electronic health-related record associated with a given individual, wherein each electronic health-related record is created by a health-care provider, and wherein the secure communication is absent a request for registering the given individual with the health care patient portal;
   for each secure communication of the plurality of secure communications:
      analyzing a set of user profiles associated with the patient portal based on patient identifying information from the at least one electronic health-related record, wherein the analyzing comprises comparing at least the patient identifying information from the secure communication to one or more user profiles associated with registered users;
      determining that an account for the health care patient portal fails to be associated with the given individual based on the one or more user profiles failing to comprise data corresponding to at the least patient identifying information;
      automatically registering, based on the determining, the given individual with the health care patient portal, wherein automatically registering the given individual comprises at least generating a user profile for the given individual based at least on the patient identifying information and the at least one electronic health-related record within the secure communication, and wherein automatically registering the given individual enables the given individual to manage and share electronic health-related records associated with the given individual;
      generating and storing a patient portal record comprising at the least patient identifying information from the at least one electronic health-related record of the secure communication, the patient portal record being presentable to a user in a standardized format; and
      automatically sending a communication to at least one of the health-related information source and the given individual, wherein the communication notifies the at least one of the health-related information source and the given individual that the given individual has been automatically registered with the health care patient portal;

storing each of the patient portal records in one of a plurality of portions of memory based on a source type associated with a source of the electronic health-related record from which the patient portal record was generated, wherein patient portal records generated from electronic health-related records provided by a user source type are stored in a first portion of the memory dedicated to user provided electronic health-related data associated with the user, wherein patient portal records generated from electronic health-related records associated with a registered entity source type are stored in a second portion of the memory dedicated to electronic health-related data provided by entities registered with the patient portal, and wherein patient portal records generated from electronic health-related records associated with a non-registered entity source type are stored in a third portion of the memory dedicated to electronic health-related data provided by entities that are not registered with the patient portal;

identifying a plurality of separate areas within a customizable user interface of the patient portal, wherein each separate area of the plurality of separate areas is assigned to a different one of the first portion of the memory, second portion of the memory, and third portion of the memory;

selecting one or more of the patient portal records for display in one of the separate areas of the customizable user interface according to which of the plurality of portions of memory the one or more patient portal records were accessed from; and presenting, based on the selecting, each of the one or more patient portal records to the given individual in the customizable user interface of the patient portal, wherein each of the one or more patient portal records is presented with at least an indication of the source type associated with the patient portal record, and wherein patient portal records from the first portion of the memory are displayed in a first separate area of the plurality of separate areas, patient portal records from the second portion of the memory are displayed in a second separate area of the plurality of separate areas, and patient portal records from the third portion of the memory are displayed in a third separate area of the plurality of separate areas, wherein patient portal records associated with the given individual and provided by user source type entities, registered source type entities, and non-registered source type entities are directly reachable from the customizable user interface by simultaneously presenting the first separate area, the second separate area, and the third separate area within the customizable user interface.

2. The information processing system of claim 1, wherein automatically registering the given individual further comprises:

automatically generating at least one of a patient portal login identifier and a patient portal login password for the given individual.

3. The information processing system of claim 2, wherein the communication sent to the at least one of the health-related information source and the given individual comprises at least the patient portal login identifier, the patient portal login password, and a uniform resource locator pointing to the health care patient portal.

4. The information processing system of claim 1, wherein at least one secure communication of the plurality of secure communications is received at a DIRECT messaging address of the health care patient portal.

5. The information processing system of claim 1, wherein automatically registering the given individual further comprises: mapping the user profile of the given individual to at least one profile associated with at least one of a health care facility associated with the secure communication and the health-related information source.

6. A computer program storage product for automatically generating a patient presence at a patient portal residing on an information processing system, the computer program storage product comprising instructions configured to perform a method comprising:

electronically communicating with a plurality of health-related information sources via at least one external information processing system;

determining, in response to electronically communicating with the plurality of health-related information source and for each health-related information source of the plurality of health-related information sources, if the health-related information source is registered with the patient portal;

in response to determining that the health-related information source fails to be registered with the patient portal, generating a first security token indicating that the health-related information source is not registered with the patient portal, and further providing the first security token to the health-related information source;

in response to determining that the health-related information is registered with the patient portal, generating a second security token indicating that the health-related information source is registered with the patient portal, and further providing the second security token to the health-related information source;

receiving, a plurality of secure communications from the plurality of health-related information sources utilizing one of the first security token or the second security token provided to each health-related information source of the plurality of health-related information sources, where each secure communication of the plurality of secure communications comprises at least one electronic health-related record associated with a given individual, wherein each electronic health-related record is created by a health-care provider and comprises at least patient identifying information associated with the given individual, where at least two of the electronic health-related records comprise different record formats, and wherein the secure communication is absent a request for registering the given individual with the patient portal;

for each secure communication of the plurality of secure communications:

analyzing a set of user profiles associated with the patient portal based on the patient identifying information, wherein the analyzing comprises comparing the at least patient identifying information from the secure communication to one or more user profiles associated with registered users;

determining that an account for the patient portal fails to be associated with the given individual based on the one or more user profiles failing to comprise data corresponding to the at least patient identifying information;

automatically registering, based on the determining, the given individual with the patient portal, wherein the automatically registering comprises at least generating a user profile for the given individual based at least on the patient identifying information within the secure communication;

generating and storing a patient portal record comprising the at least patient identifying information from the at least one electronic health-related record of the secure communication, the patient portal record being presentable to a user in a standardized format; and automatically sending a communication to at least the given individual, wherein the communication notifies the given individual that the given individual has been automatically registered with the patient portal;

storing each of the patient portal records in one of a plurality of portions of memory based on a source type associated with each electronic health-related record from which each patient portal record was generated, wherein patient portal records generated from electronic health-related records provided by a user source type are stored in a first portion of the memory dedicated to user provided electronic health-related data associated with the user, wherein patient portal records generated from electronic health-related records associated with a registered entity source type are stored in a second portion of the memory dedicated to electronic health-related data provided by entities registered with the patient portal, and wherein patient portal records generated from electronic health-related records associated with a non-registered entity source type are stored in a third portion of the memory dedicated to electronic health-related data provided by entities that are not registered with the patient portal;

identifying a plurality of separate areas within a customizable user interface of the patient portal, wherein each separate area of the plurality of separate areas is assigned to a different one of the first portion of the memory, second portion of the memory, and third portion of the memory;

selecting one or more of the patient portal records for display in one of the separate areas of the customizable user interface according to which of the plurality portions of memory the one or more patient portal records were accessed from; and presenting, based on the selecting, each of the one or more patient portal records to the given individual in the customizable user interface of the patient portal, wherein each of the one or more patient portal records is presented with at least an indication of the source type associated with the patient portal record, and wherein patient portal records from the first portion of the memory are displayed in a first separate area of the plurality of separate areas, patient portal records from the second portion of the memory are displayed in a second separate area of the plurality of separate areas, and patient portal records from the third portion of the memory are displayed in a third separate area of the plurality of separate areas, wherein patient portal records associated with the given individual and provided by user source type entities, registered source type entities, and non-registered source type entities are directly reachable from the customizable user interface by simultaneously presenting the first separate area, the second separate area, and the third separate area within the customizable user interface.

7. The computer program storage product of claim 6, wherein the secure communication is an email message addressed to a DIRECT messaging address of the patient portal.

8. The computer program storage product of claim 6, wherein the secure communication further comprises health-related data associated with the given individual.

9. The computer program storage product of claim 8, wherein one or more of the patient identifying information and health-related data are included within the secure communication as one of structured and unstructured data.

10. The computer program storage product of claim 6, wherein automatically registering the given individual further comprises:
automatically generating at least one of a patient portal login identifier and a patient portal login password for the given individual.

11. The computer program storage product of claim 10, wherein the communication sent to the given individual comprises at least the patient portal login identifier, the patient portal login password, and a uniform resource locator pointing to the patient portal.

12. The computer program storage product of claim 6, wherein the method further comprises:
determining, based on receiving the secure communication, if a health care facility associated with the secure communication has not been previously registered with the patient portal; and
based on determining that the health care facility has not been previously registered with the patient portal, automatically registering the health care facility based on information within the secure communication.

13. A method, by an information processing system comprising a patient portal, for automatically generating a patient presence at the patient portal, the method comprising:
receiving a plurality of secure communications from a plurality of health-related information sources via one or more external information processing systems, where each secure communication of the plurality of secure communications comprises at least one electronic health-related record associated with a given individual, wherein each electronic health-related record is created by a health-care provider, and wherein the secure communication is absent a request for registering the given individual with the health care patient portal;

for each secure communication of the plurality of secure communications:
analyzing a set of user profiles associated with the patient portal based on patient identifying information from the at least one electronic health-related record, wherein the analyzing comprises comparing at least the patient identifying information from the secure communication to one or more user profiles associated with registered users;
determining that an account for the health care patient portal fails to be associated with the given individual based on the one or more user profiles failing to comprise data corresponding to at the least patient identifying information;
automatically registering, based on the determining, the given individual with the health care patient portal, wherein automatically registering the given individual comprises at least generating a user profile for the given individual based at least on the patient identifying information and the at least one electronic health-related record within the secure communication, and wherein automatically registering the given individual enables the given individual to manage and share electronic health-related records associated with the given individual;

generating and storing a patient portal record comprising at the least patient identifying information from the at least one electronic health-related record of the secure communication, the patient portal record being presentable to a user in a standardized format; and automatically sending a communication to at least one of the health-related information source and the given individual, wherein the communication notifies the at least one of the health-related information source and the given individual that the given individual has been automatically registered with the health care patient portal;

storing each of the patient portal records in one of a plurality of portions of memory based on a source type associated with a source of the electronic health-related record from which the patient portal record was generated, wherein patient portal records generated from electronic health-related records provided by a user source type are stored in a first portion of the memory dedicated to user provided electronic health-related data associated with the user, wherein patient portal records generated from electronic health-related records associated with a registered entity source type are stored in a second portion of the memory dedicated to electronic health-related data provided by entities registered with the patient portal, and wherein patient portal records generated from electronic health-related records associated with a non-registered entity source type are stored in a third portion of the memory dedicated to electronic health-related data provided by entities that are not registered with the patient portal;

identifying a plurality of separate areas within a customizable user interface of the patient portal, wherein each separate area of the plurality of separate areas is assigned to a different one of the first portion of the memory, second portion of the memory, and third portion of the memory;

selecting one or more of the patient portal records for display in one of the separate areas of the customizable user interface according to which of the plurality of portions of memory the one or more patient portal records were accessed from; and presenting, based on the selecting, each of the one or more patient portal records to the given individual in the customizable user interface of the patient portal, wherein each of the one or more patient portal records is presented with at least an indication of the source type associated with the patient portal record, and wherein patient portal records from the first portion of the memory are displayed in a first separate area of the plurality of separate areas, patient portal records from the second portion of the memory are displayed in a second separate area of the plurality of separate areas, and patient portal records from the third portion of the memory are displayed in a third separate area of the plurality of separate areas, wherein patient portal records associated with the given individual and provided by user source type entities, registered source type entities, and non-registered source type entities are directly reachable from the customizable user interface by simultaneously presenting the first separate area, the second separate area, and the third separate area within the customizable user interface.

14. The method of claim 13, wherein automatically registering the given individual further comprises:
automatically generating at least one of a patient portal login identifier and a patient portal login password for the given individual.

15. The method of claim 14, wherein the communication sent to the at least one of the health-related information source and the given individual comprises at least the patient portal login identifier, the patient portal login password, and a uniform resource locator pointing to the health care patient portal.

16. The method of claim 13, wherein at least one secure communication of the plurality of secure communications is received at a DIRECT messaging address of the health care patient portal.

17. The method of claim 13, wherein automatically registering the given individual further comprises:
mapping the user profile of the given individual to at least one profile associated with at least one of a health care facility associated with the secure communication and the health-related information source.

* * * * *